United States Patent
She et al.

(10) Patent No.: US 8,835,875 B2
(45) Date of Patent: Sep. 16, 2014

(54) DETECTION APPARATUS AND DETECTION METHOD

(75) Inventors: Jun She, Shanghai (CN); Levinus Pieter Bakker, Shanghai (CN); Cornelis Reinder Ronda, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 54 days.

(21) Appl. No.: 13/517,368

(22) PCT Filed: Jan. 4, 2011

(86) PCT No.: PCT/IB2011/050008
§ 371 (c)(1), (2), (4) Date: Jun. 20, 2012

(87) PCT Pub. No.: WO2011/089532
PCT Pub. Date: Jul. 28, 2011

(65) Prior Publication Data
US 2012/0273697 A1    Nov. 1, 2012

(30) Foreign Application Priority Data
Jan. 19, 2010    (CN) .......................... 2010 1 0004754

(51) Int. Cl.
*G01N 21/64* (2006.01)
*G01N 21/33* (2006.01)
*G01N 21/29* (2006.01)
*G01N 33/18* (2006.01)

(52) U.S. Cl.
CPC ............ *G01N 33/1826* (2013.01); *G01N 21/33* (2013.01); *G01N 21/293* (2013.01); *C02F 2201/326* (2013.01)
USPC ...................................................... 250/461.1

(58) Field of Classification Search
USPC ...................................................... 250/461.1
See application file for complete search history.

(56) References Cited

U.S. PATENT DOCUMENTS

| | | | |
|---|---|---|---|
| 4,201,916 A | 5/1980 | Ellner | |
| 6,084,250 A | 7/2000 | Justel et al. | |
| 6,162,406 A | 12/2000 | Michael | |
| 6,398,970 B1 | 6/2002 | Justel et al. | |
| 7,479,641 B2 | 1/2009 | Wong | |
| 2003/0076028 A1 | 4/2003 | Nieda et al. | |
| 2007/0053208 A1 | 3/2007 | Justel et al. | |

FOREIGN PATENT DOCUMENTS

| | | |
|---|---|---|
| EP | 1857416 A2 | 11/2007 |
| GB | 1105975 A | 3/1968 |
| WO | 2009150582 A1 | 12/2009 |

*Primary Examiner* — David Porta
*Assistant Examiner* — Hugh H Maupin

(57) ABSTRACT

To overcome the disadvantages introduced by using UV sensors to detect the intensity of UV light in water purification apparatuses, a novel detection apparatus to "visualize" the quality of water in the form of visible light, instead of digitizing the intensity of UV light includes s a first detection window, coated with a first material for converting a received first ultraviolet light into a first visible light. The first ultraviolet light is emitted from an ultraviolet light source and traverses the liquid, and the detection apparatus further mixes the first visible light with second visible light to generate a third visible light. The different color of the third visible light can represent the different quality of the water.

15 Claims, 5 Drawing Sheets

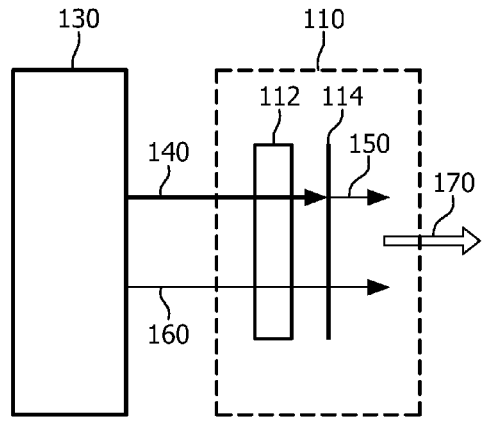
FIG. 1a
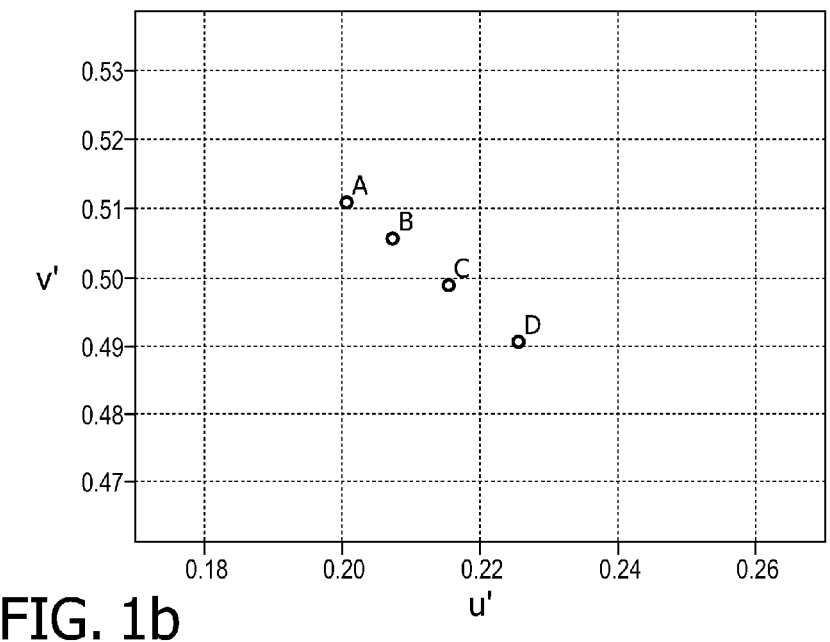
FIG. 1b
| | U' | V' | UV254(cm$^{-1}$) | $I_{UV}$ | R | G | B | Colorbar | Water quality |
|---|---|---|---|---|---|---|---|---|---|
| A | 0.201 | 0.511 | 0 | 1 | 224 | 255 | 178 | | Pure |
| B | 0.207 | 0.505 | 0.02 | 0.8 | 224 | 239 | 178 | | Good |
| C | 0.216 | 0.499 | 0.06 | 0.6 | 224 | 219 | 178 | | Poor |
| D | 0.226 | 0.490 | 0.13 | 0.4 | 224 | 201 | 178 | | Bad |
FIG. 1c

DETECTION APPARATUS AND DETECTION METHOD

FIELD OF THE INVENTION

This application relates to apparatus and methods for detecting the quality of a liquid, in particular, detection apparatus and purification apparatus utilizing ultraviolet light.

BACKGROUND OF THE INVENTION

With reference to the existing technology, ultraviolet light is widely used in detection/purification/sterilization apparatus. In these apparatus, the intensity of the UV light passing through water or any other liquid, is detected at the reactor wall of the apparatus and compared with a known intensity of the UV light generated by an UV lamp. To detect the intensity of the UV light, normally an electronic UV sensor and an appropriate power arrangement, especially an external power source, are necessary. However, the UV sensor and the power arrangement are costly and inconvenient in terms of use and maintenance. There is a need to mitigate, even overcome, the drawbacks of the current UV sensor systems.

SUMMARY OF THE INVENTION

One objective of the invention is to provide a detection apparatus which does not use the UV sensor to detect the intensity of UV light. The apparatus can be used in any liquid detection/purification/sterilization apparatus.

Another objective of the invention is to provide an apparatus and method for simply showing the quality of a target liquid by means of the color of visible light.

According to an embodiment of the invention, an apparatus for detecting the quality of a liquid is provided. The apparatus comprises a first detection window, coated with a first material for converting a received first ultraviolet light into a first visible light emitted by an ultraviolet light source and traversing the liquid, and the apparatus further mixes the first visible light with a second visible light to generate a third visible light.

The basic idea of the invention is to utilize the impact of the quality of the liquid on the transmission of the UV light in the liquid and display the impact by means of visible light. It is the quality of the liquid, for example, the compounds, pollutants, and microorganisms in the water, that determines whether the UV light is absorbed or blocked and thus influences the intensity of the UV light arriving at the first detection window, thereby also impacting the intensity of the generated first visible light. The first visible light is mixed with the second visible light, whose intensity is normally substantially independent of the quality of the liquid, to generate the third visible light. Since the ratio of the first visible light to the second visible light varies in dependence on the quality of the liquid, the color of the third visible light varies and can be used to show the quality of the liquid.

Optionally, the second visible light can be emitted by the ultraviolet light source and traverse the liquid along substantially the same path as the first UV light. The second visible light can be selected so that its intensity is substantially independent of the quality of the liquid. This provides the advantage of eliminating the necessity of having an additional light source and a corresponding power arrangement.

In a further embodiment, the ultraviolet light source comprises an ultraviolet lamp and a coating comprising a third material for converting the UV light generated by the UV lamp into the second visible light. This will make the choice and the generation of the second visible light easier.

To more evenly mix the first and the second visible light and display the third visible light irrespective of the direction from which the user perceives it, in an embodiment, a diffuser is further provided in the apparatus to diffuse the first and the second visible light along the same directions or the same range of directions, so that the two lights can be better mixed and users perceive the same color of the third visible light irrespective of the angle at which they watch this apparatus.

For ease of association of the third visible light with the quality of the liquid, in an embodiment, a color reference indicator is provided to show the mapping between the different colors of the third visible light and the quality of the liquid. Upon perceiving the third visible light, the user can thus easily understand the quality of the liquid.

In an embodiment, in addition to the first detection window, the apparatus further comprises a second detection window coated with a second material for converting a received second UV light into the second visible light, wherein the second UV light is emitted by the UV light source and traverses the liquid along a path different from the first UV light. In this embodiment, both the first and the second visible lights are generated at or near the reactor wall. Due to the different paths, especially the different lengths of the paths, the intensity of the two UV lights can be different, which further induces the different intensity of the first and the second visible lights. Accordingly, the color of the third visible light can be changed.

To avoid harm to a user's eyes as a result of the UV light which traverses the detection window(s) and is not absorbed by the material(s), in an embodiment, a UV blocker is provided to block the UV light traversing the apparatus.

In some embodiments, detection, purification, and sterilization apparatus are provided which incorporate the apparatus described above.

These and other aspects of the invention will be apparent from and elucidated with reference to the embodiment described hereinafter in conjunction with the drawings described hereinafter.

BRIEF DESCRIPTION OF THE DRAWINGS

The above and other aspects and features of the present invention will become more apparent from the following detailed description considered in connection with the accompanying drawings, in which:

FIG. 1a depicts, according to an embodiment of the invention, a detection apparatus together with a UV light source;

FIGS. 1b and 1c illustrate, according to one embodiment of the present invention, the mixing of the first and the second visible lights to generate the third visible light;

The same or similar reference numerals are used to denote same or similar parts throughout the Figures.

DETAILED DESCRIPTION OF EMBODIMENTS

Figure 2:
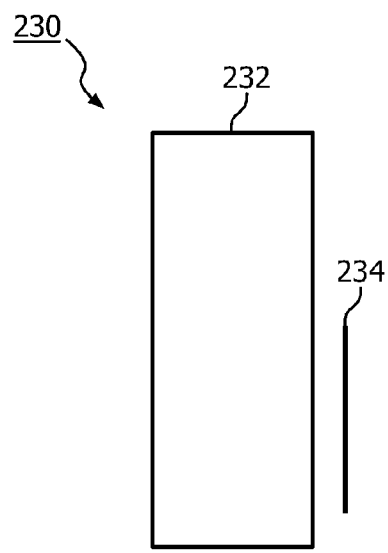
FIG. 2 depicts, according to an embodiment of the invention, a UV light source generating the UV light and visible light.

As explained before, the existing water treatment apparatus, including quality detection, purification and sterilization apparatus, use UV light and compare the intensity of the UV light received by a UV sensor with the intensity of the UV light generated by a UV lamp to analyze the quality of water. The UV sensors are normally costly and vulnerable to aging, dust and pollutants and need to be replaced accordingly. Additional power supply is necessary to feed power to the UV sensors and other necessary components, and maintaining and replacing the power arrangement, including the power source, is also costly and inconvenient.

To mitigate some of the above-mentioned drawbacks, the present invention does not utilize a UV sensor to sense the intensity of the UV light. Instead, the present invention utilizes the impact of the quality of water on the absorption of UV light and displays this impact in a visible way. As shown in the embodiment of FIG. 1, a detection apparatus 110 and a UV light source 130 are illustrated. The detection apparatus 110 comprises a detection window 112 and a coating layer 114. The coating layer 114 is capable of generating visible light when being excited by UV light. For example, the coating layer 114 can be made of or comprises phosphor to generate yellow light when being hit by the UV light. A person skilled in the art should understand that other kinds of phosphor or material can be chosen for the same purpose. The coating layer 114 can be applied to the surface of the detection window 112. A person skilled in the art should understand that the arrangement of the detection window 112 and the coating layer 114 can vary depending on the real implementation. For example, it is also an option to embed the layer 114 within the detection window 112, or the first material of the layer 114 can be dispersed within the detection window 112. The key point here is that when a UV light hits the window and the first material, the first visible light can be generated, and the intensity of the first visible light depends on the intensity of the UV light. A UV light source 130 is configured to generate UV light, which traverses the liquid and arrives at the detection apparatus 110 as the first UV light 140. The intensity of the first UV light 140 may vary due to the quality of the liquid, which is determined by for example the compounds, pollutants, and microorganisms. In other words, the UV absorption of the liquid influences the intensity of the first UV light 140. At the detection apparatus, the first UV light 140 excites the first material of the coating layer 114, which consequently generates the first visible light 150. A second visible light 160 can be received and mixed, by the detection apparatus 110, with the first visible light 150 to generate a third visible light 170. The ratio of the first visible light 150 to the second visible lights 160 determines the color of the third visible light 170. In other words, different intensities of the first and the second visible light cause the third visible light to have a different color. Then the quality of the liquid can be perceived by means of the color of the third visible light 170.

In an embodiment, the second visible light 160 can be generated by the UV light source 130 and its intensity is known beforehand. Normally the intensity of the second visible light 160 is less impacted by the compounds, pollutants, and/or microorganism of the liquid, especially in comparison with the change in intensity of the first UV light 140 travelling along the same path. FIG. 1b and FIG. 1c illustrate an embodiment of mixing the first and the second visible lights to generate a third visible light. The four points (A, B, C and D) represent four different colors of the third visible light, which further can be used to represent different quality of the water. (U', V') represent the coordinate, UV254 represents the absorption when a UV light transmitting in a liquid at the wavelength of 254 nm, $I_{uv}$ represents the normalized intensity of the UV light arriving at the detection apparatus, G represents the intensity of the first visible light (Green light) generated by the first material, and the second visible light comprises the Red light (R) and Blue light (B). When different intensities of the first visible light and the second visible light mixed, the third visible light can be represented by the color, for example as shown in the column of "colorbar". A person skilled in the art should understand that, the second visible light can be a light having a single color or wavelength, also can be a mixture of two or more lights. A person skilled in the art also should understand that, besides generating the second visible light, some UV lamps may also generate the first visible light with a pre-known intensity. For example, some UV lamps may generate Green light, which will traverse the water and mix with the Green light generated by the first material. In other word, the value of Green light shown in FIG. 1c is the mixture of the Green light generated by the UV light source and the Green light generated by the first material. However, the intensity of the Green light generated by the UV lamp per se, after traversing the water, will not be significant impacted by the different quality of the water. Therefore the major contribution of the change of the third visible light comes from the Green light generated by the first material, not the substantial constant Green light generated by the UV lamp.

In the embodiment shown in FIG. 2, the illustrated UV light source 230 comprises a UV lamp 232 capable of generating UV light, and the UV lamp 232 or part of it is coated with a third material 234 capable of generating the second visible light 160. Part of the UV light can traverse the third material 234 and penetrate into the liquid. This embodiment provides the benefits of great flexibility in choosing the color of the second visible light and determining the intensity of the second visible light, by choosing an appropriate third material. For example, the third material can be chosen to generate a blue light or red light. A person skilled in the art should understand that the area covered by the third material 234 can be varied depending on different requirements, for example, the whole UV lamp 232 can be covered, or the side of the UV lamp 232 toward the detection apparatus, or even a small area for reducing the amount of the third material. The third material can be made of phosphor, and optionally a water-proof arrangement can be placed to protect the water from the phosphor.

Figure 3:
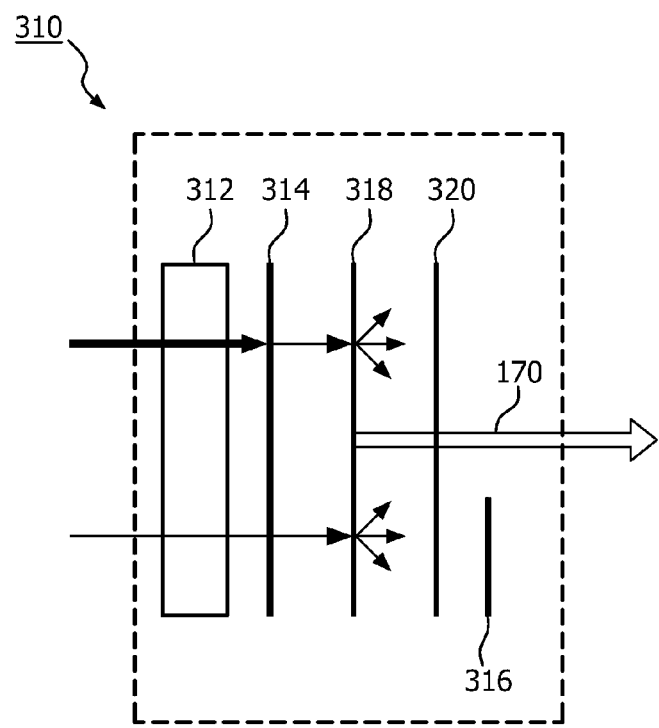
FIG. 3 depicts, according to embodiments of the invention, detection apparatus.

In order to make it easy to understand the meaning of different colors of the third visible light, in an embodiment, a color reference indicator 316 is provided in the embodiments shown in FIG. 3. The color reference indicator 316, which can be in the shape of a color bar code, color ring, color matrix, shows the mapping between a different color and a different quality of the liquid. So a user can easily determine the quality of the water, by mapping the color of the third visible light into the color reference indicator.

The first visible light 150 generated by the first material at the detection window may have a different transmission direction than the second visible light 160 arriving at the detection window from several directions, as a result of which the two visible lights may be unevenly mixed, which, when viewed, from a different angle behind the detection window, may result in the color of the third visible light 170 being perceived differently. To address this problem, in an embodiment as shown in FIG. 3, a diffuser 318 is allocated behind the detection window 312 and the coating layer 314 made of the first material, and configured to diffuse the first and the second visible lights more evenly in the substantially same transmission direction. By virtue thereof the two visible lights can be mixed better and the different color perceived from different visual angles is negligible. In another embodiment, the first material is made of nano-scale phosphor particles, which can have a second function: diffusing the second visible light. In this case, there is no need for a separate diffuser layer, the diffuser 318 actually being integrated in the coating layer. For better protecting human eyes in case part of the UV light traverses the detection window and/or the diffuser, a UV blocker 320 is provided to block UV light in order to avoid harm to human eyes. The UV blocker 320 can be placed between the detection window 312 and the diffuser 318, or behind the detection window 312 and the diffuser 318.

Figure 4A:
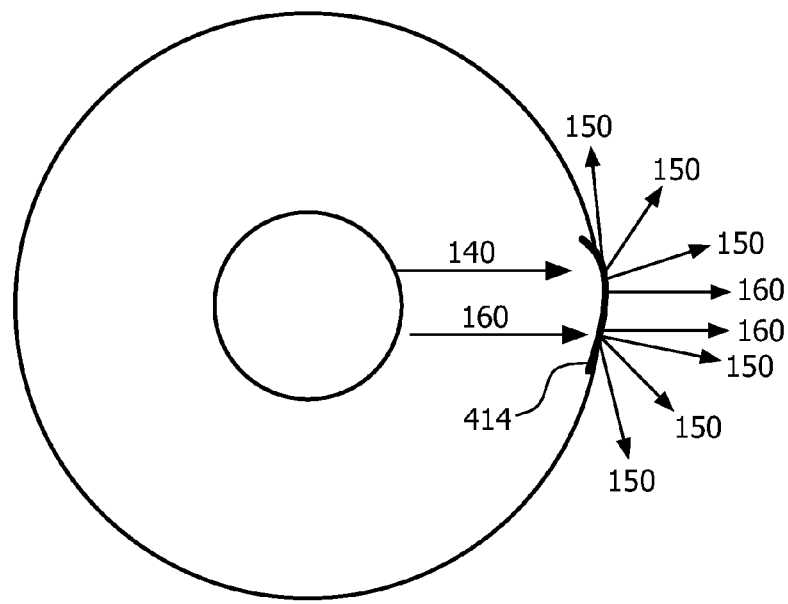
FIG. 4a depicts, according to an embodiment of the invention, a water purification apparatus without a diffusing function.
Figure 4B:
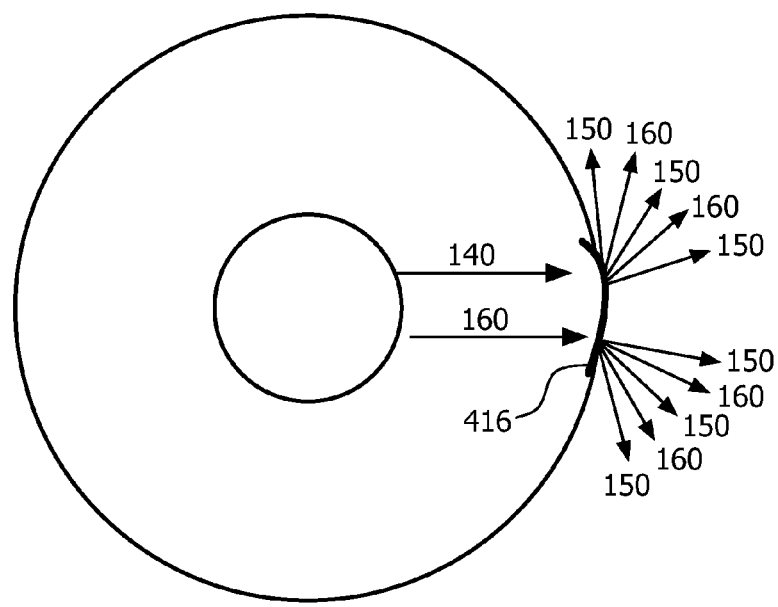
FIG. 4b depicts, according to an embodiment of the invention, a water purification apparatus using nano-scale phosphor particle as a diffuser.

FIG. 4a illustrates an embodiment in which the second visible light is not diffused, wherein the first visible light 150 generated by the first material, e.g., phosphor 414, has a wide range of transmission directions, while the second visible light 160 has a much narrower range of transmission directions. This will result in the two visible lights not being evenly mixed, and thus the third visible light shows a different color at different visual angles. p FIG. 4b illustrates an embodiment in which nano-scale phosphor particles are used to diffuse the second visible light. The nano-scale phosphor 416 not only generates the first visible light, but also diffuses the second light, so that the two visible lights are mixed more evenly. This will provide the additional advantage that an additional diffuser layer can be dispensed with.

Figure 5:
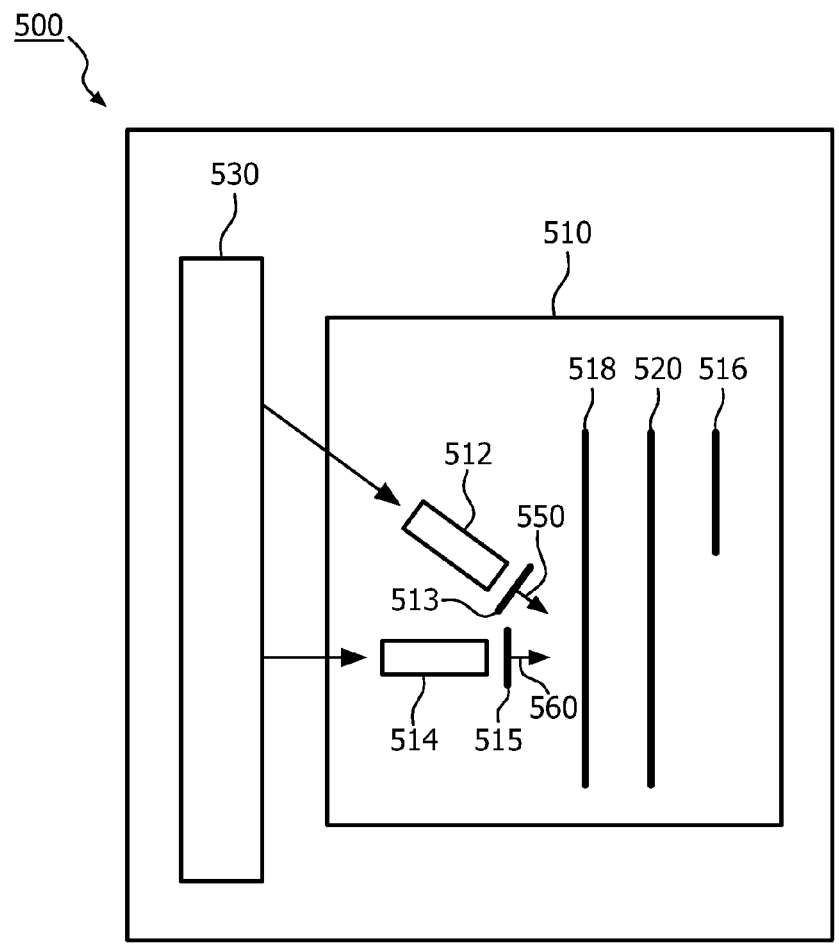
FIG. 5 depicts, according to embodiments of the invention, detection apparatus together with a UV light source.

In the above-mentioned embodiments, the first UV light and the second visible light substantially follow the same transmission paths. This is not an essential feature of the present invention. FIG. 5 illustrates another embodiment in which not only the first visible light 550 is generated by the detection apparatus 510, but also the second visible light 560 is generated by the detection apparatus 510. In the water quality detection/purification/sterilization apparatus 500, the UV light source 530 generates UV lights penetrating the liquid. The detection apparatus 510 comprises not only the first detection window 512 coated with the first material 513, but also the second detection window 514 coated with a second material 515. A person skilled in the art should understand that the placement of the first/second material and the first/second detection window is flexible depending on the specific implementation. The two different detection windows 512 and 514 are positioned at two different angles to receive different UV lights which are transmitted along different paths. Particularly, the two different paths have different lengths, so that the UV lights 542 and 544 have different intensities when arriving at the detection apparatus 510. The two materials are also different so as to generate different visible lights when excited by the received UV lights; for example, the first material is capable of generating yellow light while the second material is capable of generating blue light. Then the yellow light and the blue light are mixed by the detection apparatus 510 to generate the third, green, light. The color of the third, green, light is determined by the intensities of the yellow light and the blue light, which in turn are determined by the intensities of the UV lights, which are influenced by the quality of the liquid. Due to the different transmission paths of the two UV lights, the quality of the liquid has a different impact on the intensities of the two UV lights. The color reference indicator 516, the diffuser 518 and the UV blocker 520 are optional.

Figure 6:
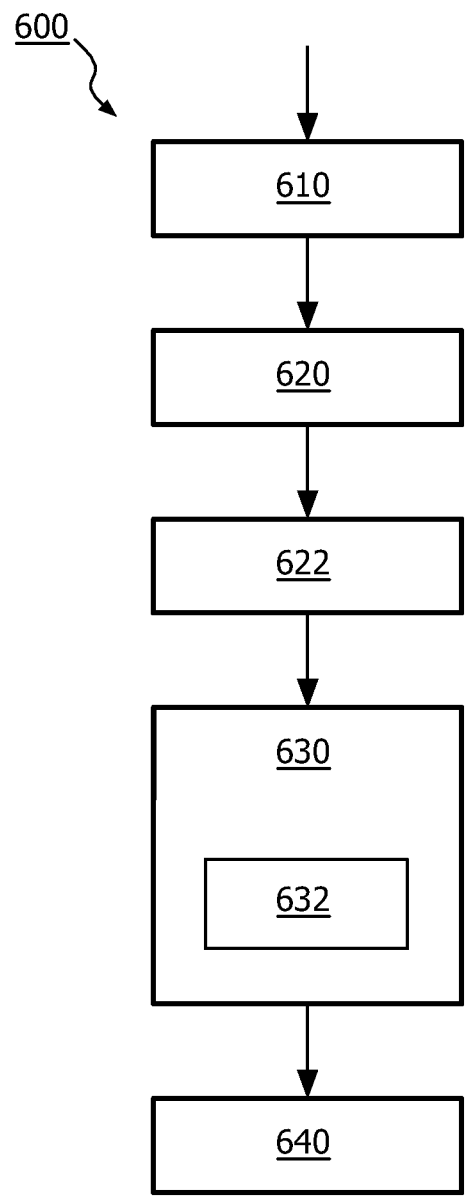
FIG. 6 illustrates, according to an embodiment of the invention, a method of detecting the quality of water.

FIG. 6 illustrates a method 600 of detecting the quality of a liquid. Method 600 comprises a step 610 of receiving a first UV light which is emitted from a UV light source and which traverses the liquid, and a step 620 of generating the first visible light by means of a first material excited by the first UV light, and a step 630 of mixing the first and the second visible lights to generate a third visible light. A different color of the third visible light represents a different quality of the liquid. Method 600 optionally comprises a step 622 of generating the second visible light by means of a third material excited by the UV light, and an optional step 632 of mixing the first and the second visible lights by means of a diffuser causing them to be transmitted along the main directions. Method 600 further comprises a step 640 of comparing the color of the third visible light with a color reference indicator so as to determine the quality of the liquid.

A skilled person should understand that the present invention is not only represented by each individual embodiment described above, and that the technical features of these embodiments can be combined to generate alternative embodiments.

It should be noted that the above-mentioned embodiments illustrate rather than limit the invention and that those skilled in the art will be able to design alternative embodiments without departing from the scope of the appended claims In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The use of the words first, second and third, et cetera, does not indicate any ordering. These words are to be interpreted as names.

What is claimed is:

1. An apparatus for detecting a quality of a liquid comprising:
   a first detection window configured to receive an ultraviolet light;
   an input configured to receive a first visible light; and
   a first material coating the window for converting the received ultraviolet light into a second visible light for mixing with the received first visible light to generate a third visible light indicative of the quality of the light, wherein the ultraviolet light is emitted from an ultraviolet light source and traverses the liquid.

2. The apparatus as claimed in claim 1, wherein a color of the third visible light is determined by an intensity of the received ultraviolet light and an intensity of the first visible light, and wherein the color indicates a absorption of the liquid.

3. The apparatus as claimed in claim 1, wherein the first visible light is emitted by the ultraviolet light source and traverses the liquid along a same path as the ultraviolet light.

4. The apparatus as claimed in claim 3, wherein the ultraviolet light source comprises an ultraviolet lamp and a coating on the ultraviolet lamp comprising a second material for converting part of the ultraviolet light generated by the ultraviolet lamp into the first visible light.

5. The apparatus as claimed in claim 1, further comprising a diffuser configured to diffuse the first and the second visible lights transmitted along same directions.

6. The apparatus as claimed in claim 1, wherein the first material is made of nano-scale phosphor particles for diffusing the first visible light.

7. The apparatus as claimed in claim 1, further comprising:
   a second detection window coated with a second material for converting a received further ultraviolet light into the first visible light, wherein the further ultraviolet light is emitted by the ultraviolet light source and traverses the liquid along a different path than the ultraviolet light.

8. The apparatus as claimed in claim 1, wherein the first and the second visible lights have a different color.

9. The apparatus claimed in claim 1, further comprising a color reference indicator including a plurality of color bars or color blocks, each color bar or color block indicating a different quality of the liquid.

10. The apparatus as claimed in claim 1, further comprising an ultraviolet light filter configured to filter the received ultraviolet light traversing the first detection windows.

11. An ultraviolet purification apparatus comprising a detecting apparatus for detecting a quality of a liquid, the detecting apparatus comprising:
 a first detection window configured to receive an ultraviolet light;
 an input configured to receive a first visible light; and
 a first material coating the window for converting the received ultraviolet light into a second visible light for mixing with the received visible light to generate a third visible light indicative of the quality of the liquid, wherein the ultraviolet light is emitted from an ultraviolet light source and traverses the liquid.

12. A method of detecting a quality of a liquid, the method comprising the acts of:
 receiving a first ultraviolet light emitted by an ultraviolet light source and traversing the liquid;
 generating a first visible light by a first material excited by the first ultraviolet light; and
 mixing the first visible light with a second visible light to generate a third visible light.

13. The method as claimed in claim 12, wherein the ultraviolet light source comprises an ultraviolet lamp and a coating on the ultraviolet lamp comprising a second material, the method further comprising the
 act of generating the second visible light by the second material being excited by the ultraviolet light generated by the ultraviolet lamp.

14. The method as claimed in claim 12, further comprising act of diffusing the first visible light and the second visible light by a diffuser transmitting the first and second visible lights along same directions.

15. The method as claimed in claim 12, further comprising the act of;
 comparing a color of the third visibly light with a color reference indicator so as to determine the quality of the liquid.

* * * * *